United States Patent
Pasupuleti et al.

(10) Patent No.: US 11,890,093 B2
(45) Date of Patent: *Feb. 6, 2024

(54) NEURAL NETWORK BASED RADIOWAVE MONITORING OF PATIENT DEGENERATIVE CONDITIONS

(71) Applicant: VENTECH SOLUTIONS, INC., Columbus, OH (US)

(72) Inventors: Ravi Kiran Pasupuleti, Triplicane Chennai (IN); Ravi Kunduru, Columbus, OH (US)

(73) Assignee: Ventech Solutions, Inc., Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/088,174

(22) Filed: Dec. 23, 2022

(65) Prior Publication Data
US 2023/0210405 A1 Jul. 6, 2023

Related U.S. Application Data

(63) Continuation of application No. 16/814,593, filed on Mar. 10, 2020, now Pat. No. 11,622,701.

(51) Int. Cl.
- *A61B 5/11* (2006.01)
- *G01S 7/41* (2006.01)
- *G06V 10/764* (2022.01)
- *G06V 10/70* (2022.01)

(Continued)

(52) U.S. Cl.
CPC ............... *A61B 5/112* (2013.01); *A61B 5/05* (2013.01); *A61B 5/1124* (2013.01); *A61B 5/1126* (2013.01); *A61B 5/1128* (2013.01); *A61B 5/4023* (2013.01); *A61B 5/7267* (2013.01);

(Continued)

(58) Field of Classification Search
CPC ....................................... A61B 5/112
See application file for complete search history.

(56) References Cited

PUBLICATIONS

Zhao, Peijun, et al. "mid: Tracking and identifying people with millimeter wave radar." 2019 15th International Conference on Distributed Computing in Sensor Systems (DCOSS). IEEE, 2019. (Year: 2019).*

(Continued)

*Primary Examiner* — Vincent Rudolph
*Assistant Examiner* — Raphael Schwartz
(74) *Attorney, Agent, or Firm* — Mahamedi IP Law LLP (57) ABSTRACT

A method and system of training a machine learning neural network (MLNN) in anatomical degenerative conditions in accordance with anatomical dynamics. The method comprises receiving, in a first input layer of the MLNN, from a millimeter wave (mmWave) radar sensing device, a first set of mmWave radar point cloud data representing a first gait characteristic of a subject in motion, comprising an arm swing velocity, receiving, in a second layer, a second set of mmWave radar point cloud data representing a second gait characteristic comprising a measure of dynamic postural stability, the input layers being interconnected with an output layer of the MLNN via an intermediate layer, and training a MLNN classifier in accordance with a classification that increases a correlation between a degenerative condition of the subject as generated at the output layer and the sets of mmWave point cloud data.

20 Claims, 4 Drawing Sheets

(51) Int. Cl.
*A61B 5/05* (2021.01)
*A61B 5/00* (2006.01)

(52) U.S. Cl.
CPC .............. *G01S 7/415* (2013.01); *G01S 7/417* (2013.01); *G06V 10/70* (2022.01); *G06V 10/764* (2022.01)

(56) References Cited

PUBLICATIONS

Hu, Kun, et al. "Graph sequence recurrent neural network for vision-based freezing of gait detection." IEEE Transactions on Image Processing 29 (2019): 1890-1901. (Year: 2019).*

* cited by examiner

Receiving, in a first input layer of the MLNN, from a millimeter wave (mmWave) radar sensing device, a first set of mmWave radar point cloud data representing a first gait characteristic of the subject

310

Receiving, in at least a second layer of the MLNN, from the mmWave radar sensing device, an at least a second set of mmWave radar point cloud data representing an at least a second gait characteristic of the subject, the first and the at least a second input layers being interconnected with an output layer of the MLNN via at least one intermediate layer, the at least one intermediate layer configured in accordance with an initial matrix of weights, the first, at least a second, intermediate and output layers of the MLNN being implemented, using the one or more processors, in a memory of the computing device

320

Training a MLNN classifier in accordance with a supervised classification that establishes a correlation between a degenerative condition of the subject as generated at the output layer and the first and at least a second sets of mmWave point cloud data

330

Adjusting the initial matrix of weights by backpropagation thereby to increase the correlation between the degenerative condition and the first and at least a second sets of mmWave point cloud data

Deploying the trained MLNN classifier upon receiving, in relation from a subsequent subject in motion, subsequent mmWave point cloud data at the first input layer and the at least a second input layer in association with the trained MLNN

410

Generating, at the output layer, a likelihood of the degenerative condition as being attributable to the subsequent subject

NEURAL NETWORK BASED RADIOWAVE MONITORING OF PATIENT DEGENERATIVE CONDITIONS

RELATED APPLICATION

This application is a continuation of, and claims the benefit of priority to, U.S. patent application Ser. No. 16/814,593 filed Mar. 10, 2022; the aforementioned priority application being hereby incorporated by reference in its entirety.

TECHNICAL FIELD

The disclosure herein relates to neural network systems for monitoring anatomical gait dynamics in diagnosis of anatomical degenerative conditions.

BACKGROUND

Despite improvements in medical industry and healthcare, the incidence of neurodegenerative and muscular degenerative diseases and disorders remains a common concern for patients as aging progresses. Typically, onset and progression of neurodegenerative and muscular degenerative diseases and disorders manifest in abnormal gait patterns in a human subject. Existing approaches typically depend upon physical presence of a doctor or a physician for assessment and detection of gait abnormalities in patients. For example, the use of interview tools in accordance with a pre-designed questionnaire between doctor and patient captures responses from the patient during an interview. Such approaches have inherent shortcomings for detection of gait abnormality in relation to onset and progression of neurodegenerative and muscular degenerative diseases and disorders.

DETAILED DESCRIPTION

Methods and systems provided herein, among other advantages and benefits, to apply millimeter wave (mmWave) radar radio-frequency (RF) based sensing technologies to monitor abnormal anatomical gait patterns and their correlations with progression of degenerative neurological and muscular disorders and conditions. In particular, via supervised training of a neural network in correlating gait patterns and posture patterns of a human subject, based on mmWave radar sensing. For recognizing the gait patterns, the system is subjected to a supervised training regimen. During the training, one or more features corresponding to various gait characteristics are observed and correlated with point cloud data of subjects having known gait patterns associated with the various neurological and muscular dystrophy conditions or disorders. Measurable or observable features and characteristics corresponding to the gait patterns can include motion, posture, arm swing velocity and body balance with regard to both upper body and lower body of human subjects, in embodiments. In embodiments, motion vectors and posture vectors are computed based on sensed mmWave point cloud data representing observed upper and lower body members and body segments of the subjects exhibiting known gait patterns, and gait features representing gait dynamics are derived from observed time series of swing intervals and stance intervals of the left and right lower body members. Advantageously, upon deployment, the trained machine learning neural network is capable of ascertaining abnormal gait patterns in predicting neurodegenerative and muscular degenerative disorders.

Millimeter wave radar sensing technology as described and applied herein refers to detection of objects and providing information on range, velocity and angle of those objects. mmWave radar uses a contactless technology which operates in the spectrum between 30 GHz and 300 GHz, having inherent small wavelengths that provide sub-mm range accuracy while able to penetrate materials such as plastic, drywall, clothing, and being impervious to environmental conditions like rain, fog, dust and snow. As opposed to commercial radar techniques, the disclosure herein implements a high-resolution mmWave radar sensor to obtain a relatively richer radar point cloud representation for tracking and monitoring of a medical patient anatomical features, limbs and extremities. Advantageously, in embodiments implemented herein, 60-GHz mmWave sensors provide 4 GHz of UWB bandwidth, resulting in 16 times the available bandwidth than 24-GHz sensors for high-accuracy mmWave radar applications.

As referred to herein, a point cloud refers to a set of data points in space. As the output of 3D scanning processes, in this case a mmWave 3D scanning and sensing operations, point clouds are used to capture anatomical feature data of the human subject. mm Wave radar, based on the principle of frequency modulated continuous wave (FMCW) radar, has the ability to simultaneously measure range and relative radial speed of a target point. A mmWave radar sensor is applied herein to produce point clouds, of varying density of data points in some embodiments, by making repeated measurements as the body and body members of a medical patient or subject moves, each time acquiring the data from a different viewpoint or perspective. Mm Wave sensor devices transmit an RF signal and record reflection from the target point that is collected in the point cloud, the point cloud data including an object range, angle, velocity, signal strength delivered, and optionally a pre-designated subject ID in one embodiment, over a computing and communication interface. The subject ID may be a patient ID in some embodiments.

As described herein, the neural networks, in embodiments, refer to an artificial intelligence (AI) based neural network having interconnected nodes, and assemblies of nodes, representing layers of the neural network, including machine learning (ML) or deep learning (DL) models. In a particular embodiment, the ML or neural network model herein may be implemented as a convolution neural network (CNN).

In accordance with a first example embodiment, provided is a method of training a machine learning neural network (MLNN) in monitoring anatomical dynamics of a subject in motion. The method is performed in one or more processors of a computing device and comprises receiving, in a first input layer of the MLNN, from a millimeter wave (mmWave) radar sensing device, a first set of mmWave radar point cloud data representing a first gait characteristic of the subject; receiving, in at least a second layer of the MLNN, from the mmWave radar sensing device, an at least a second set of mmWave radar point cloud data representing an at least a second gait characteristic of the subject, the first and the at least a second input layers being interconnected with an output layer of the MLNN via at least one intermediate layer, the at least one intermediate layer configured in accordance with an initial matrix of weights, the first, at least a second, intermediate and output layers of the MLNN being implemented, using the one or more processors, in a memory of the computing device; training a MLNN classifier in accordance with a supervised classification that establishes a correlation between a degenerative condition of the subject as generated at the output layer and the first and at least a second sets of mmWave point cloud data; and adjusting the initial matrix of weights by backpropagation thereby to increase the correlation between the degenerative condition and the first and at least a second sets of mmWave point cloud data.

In embodiments, the backpropogation comprises recursively adjusting the initial matrix of weights in diminishment of an error matrix calculated at the output layer thereby to increase the correlation between the degenerative condition and the first and at least a second sets of mmWave point cloud data.

In some aspects, the first and the at least a second gait characteristics are characterized in accordance with at least one of: gait rhythmicity, bilateral stepping coordination, step length scaling, arm swing coordination, arm swing velocity and dynamic postural stability.

In some embodiments, the first and the at least a second gait characteristics are monitored via the mmW radar sensor device for the subject in motion, where the motion includes at least one of: alterations in gait speed, head turns of the subject, avoiding an obstacle by walking around, avoiding an obstacle by stepping over, ascending and descending steps, walking on a bare surface along a corridor, walking on a covered surface along a corridor, and motion in performance of functional mobility tasks in a residence environment.

In some aspects, the gait characteristics are classified in accordance with at least one of: a hemiplegic gait, a diplegic gait, a neuropathic gait, a myopathic gait, a choreiform gait, an ataxic gait, a Parkinsonian gait, a reduced gait and a sensory gait.

In embodiments, to the degenerative condition of the subject comprises at least one of a neurodegenerative condition and a muscular dystrophy condition.

In an embodiment, the mmWave radar sensing device comprises a 60 GHz mmWave radar sensing device.

In some aspects, the method further comprises deploying the trained MLNN classifier upon establishing that the correlation with the degenerative condition exceeds a 90 percent threshold value.

In yet other embodiments, the method further comprises deploying the trained MLNN classifier upon receiving, in relation from a subsequent subject in motion, subsequent mmWave point cloud data at the first input layer and the at least a second input layer in association with the trained MLNN.

In one aspect, the method further comprises generating, at the output layer, a likelihood of the degenerative condition as being attributable to the subsequent subject.

In accordance with a second example embodiment, a non-transitory medium storing instructions executable in a processor of a server computing device is provided. The instructions, when executed in one or more processors, cause operations comprising receiving, in a first input layer of the MLNN, from a millimeter wave (mmWave) radar sensing device, a first set of mmWave radar point cloud data representing a first gait characteristic of the subject; receiving, in at least a second layer of the MLNN, from the mmWave radar sensing device, an at least a second set of mmWave radar point cloud data representing an at least a second gait characteristic of the subject, the first and the at least a second input layers being interconnected with an output layer of the MLNN via at least one intermediate layer, the at least one intermediate layer configured in accordance with an initial matrix of weights, the first, at least a second, intermediate and output layers of the MLNN being implemented, using the one or more processors, in a memory of the computing device; training a MLNN classifier in accordance with a supervised classification that establishes a correlation between a degenerative condition of the subject as generated at the output layer and the first and at least a second sets of mmWave point cloud data; and adjusting the initial matrix of weights by backpropagation thereby to increase the correlation between the degenerative condition and the first and at least a second sets of mmWave point cloud data.

In accordance with a third example embodiment, a computing system implements a machine learning neural network (MLNN) in monitoring anatomical gait dynamics in patient degenerative conditions. The computing system, which in embodiments can an edge computing device or a server computing device, includes one or more processors and a memory storing instructions, which, when executed in the one or more processors causing operations comprising receiving, in a first input layer of the MLNN, from a millimeter wave (mmWave) radar sensing device, a first set of mmWave radar point cloud data representing a first gait characteristic of the subject; receiving, in at least a second layer of the MLNN, from the mmWave radar sensing device, an at least a second set of mmWave radar point cloud data representing an at least a second gait characteristic of the subject, the first and the at least a second input layers being interconnected with an output layer of the MLNN via at least one intermediate layer, the at least one intermediate layer configured in accordance with an initial matrix of weights, the first, at least a second, intermediate and output layers of the MLNN being implemented, using the one or more processors, in the memory; training a MLNN classifier in accordance with a supervised classification that establishes a correlation between a degenerative condition of the subject as generated at the output layer and the first and at least a second sets of mmWave point cloud data; and adjusting the initial matrix of weights by backpropagation thereby to increase the correlation between the degenerative condition and the first and at least a second sets of mmWave point cloud data.

One or more embodiments described herein provide that methods, techniques, and actions performed by a computing device are performed programmatically, or as a computer-implemented method. Programmatically, as used herein, means through the use of code or computer-executable instructions. These instructions can be stored in one or more memory resources of the computing device.

Furthermore, one or more embodiments described herein may be implemented through the use of logic instructions that are executable by one or more processors of a computing device, including a server computing device. These instructions may be carried on a computer-readable medium. In particular, machines shown with embodiments herein include processor(s) and various forms of memory for storing data and instructions. Examples of computer-readable mediums and computer storage mediums include portable memory storage units, and flash memory. A server computing device as described herein utilizes processors, memory, and logic instructions stored on computer-readable medium. Embodiments described herein may be implemented in the form of computer processor-executable logic instructions or programs stored on computer memory mediums.

System Description

Figure 1:
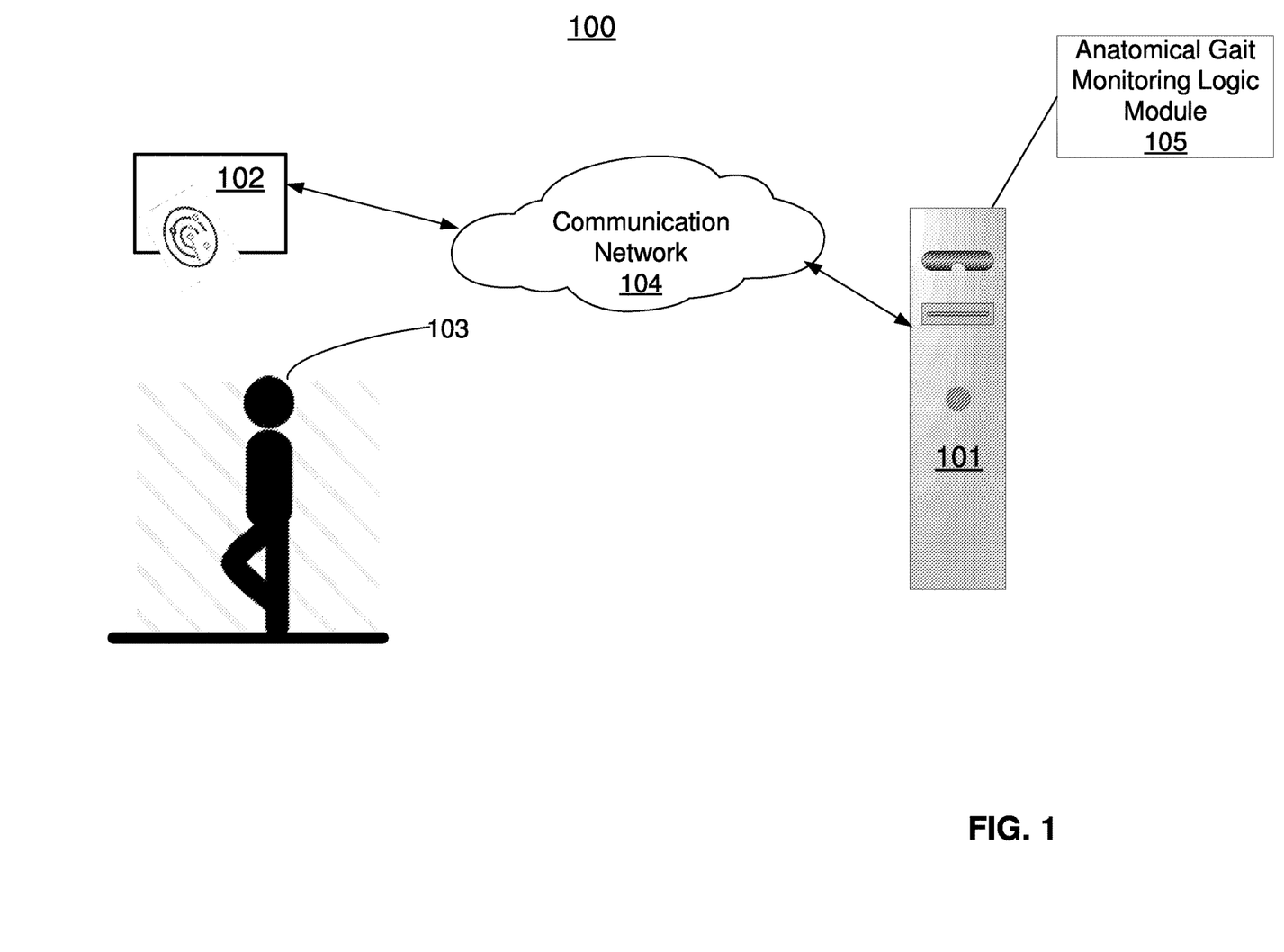
FIG. 1 illustrates, in an example embodiment, a system for training a machine learning neural network (MNLL) in monitoring anatomical gait characteristics.

FIG. 1 illustrates, in an example embodiment, system 100 for training a machine learning neural network (MNLL) in monitoring anatomical gait characteristics. Server computing system or server device 101, also referred to herein as server 101, includes anatomical gait monitoring logic module 105 embodied according to computer processor-executable instructions stored within a non-transitory memory. Server 101 is in communication via communication network 104 with mmWave sensing and communication device 102, sensing and monitoring anatomical gait characteristics of medical patient 103 during walking. In some embodiments, mmWave sensing and communication device 102 can be configured of multiple mmWave sensors working in coordination.

Figure 2:
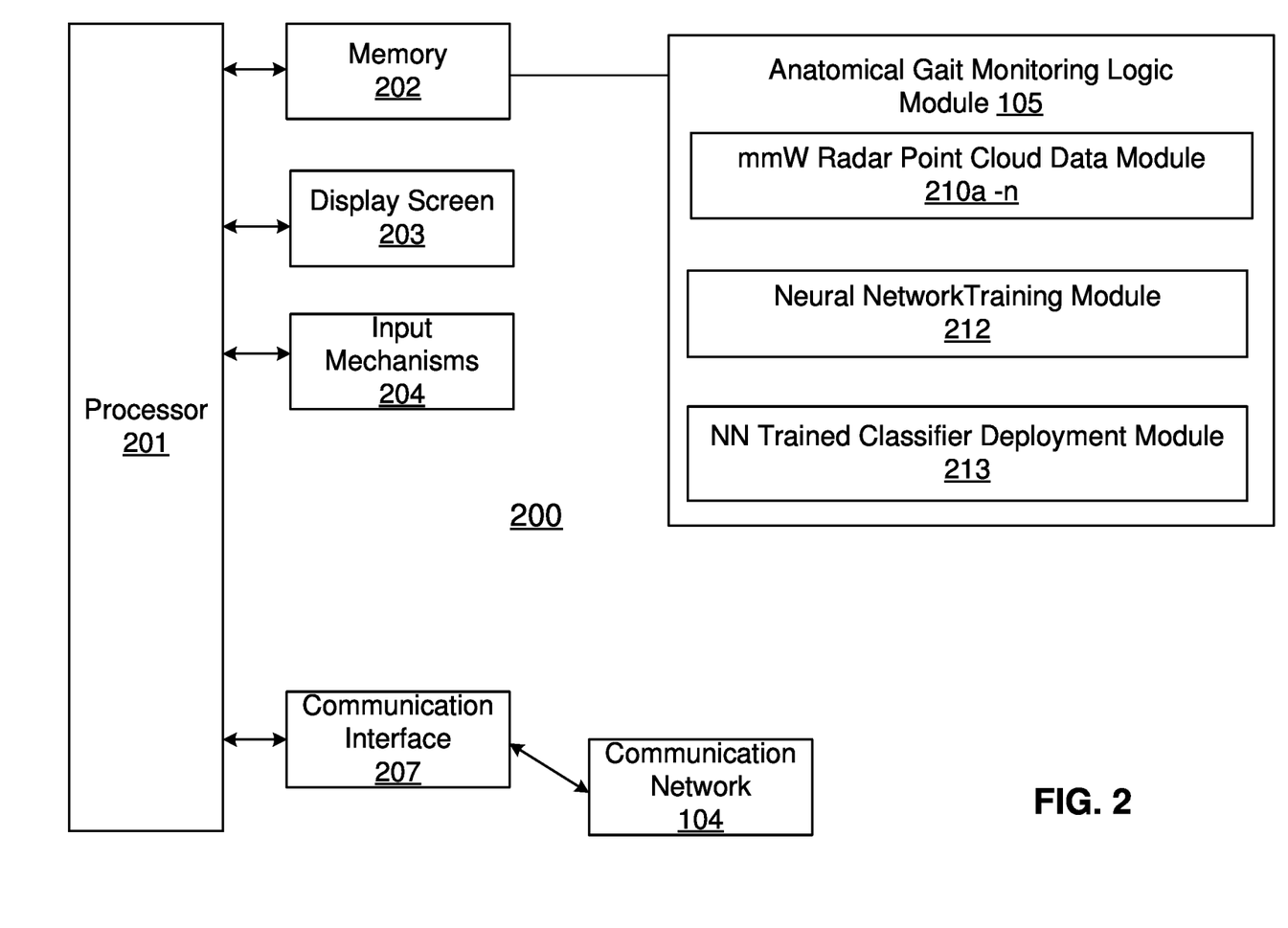
FIG. 2 illustrates, in one example embodiment, an architecture of a system for training a machine learning neural network (MNLL) in monitoring anatomical gait characteristics.

FIG. 2 illustrates, in one example embodiment, an architecture of a system 200 for training a machine learning neural network (MNLL) in monitoring anatomical gait characteristics. Server computing system or device 101, also referred to herein as server 101, may include processor 201, memory 202, display screen 203, input mechanisms 204 such as a keyboard or software-implemented touchscreen input functionality, and communication interface 207 for communicating via communication network 104. Memory 202 may comprise any type of non-transitory system memory, storing instructions that are executable in processor 201, including such as a static random access memory (SRAM), dynamic random access memory (DRAM), synchronous DRAM (SDRAM), read-only memory (ROM), or a combination thereof.

Anatomical gait monitoring logic module 105 includes processor-executable instructions stored in memory 202 of server 101, the instructions being executable in processor 201. Anatomical gait monitoring logic module 105 can comprise portions corresponding to sub-modules including mmWave radar point cloud data module 210a-n, neural network training module 212, and neural network trained classifier deployment module 213.

Processor 201 uses executable instructions of mmWave radar point cloud data module 210a-n to receive, in a first input layer of the MLNN, from a millimeter wave (mmWave) radar sensing device, a first set of mmWave radar point cloud data representing a first gait characteristic of the subject. Processor 201 also uses executable instructions of mmWave radar point cloud data module 210a-n to receive, in at least a second layer of the MLNN, from the mmWave radar sensing device, an at least a second set of mmWave radar point cloud data representing an at least a second gait characteristic of the subject. The first and the at least a second input layers being interconnected with an output layer of the MLNN via at least one intermediate layer, the at least one intermediate layer configured in accordance with an initial matrix of weights, the first, at least a second, intermediate and output layers of the MLNN being implemented, using the one or more processors, in a memory of the computing device. Data module 210a-n can be configured with variable quantities of input layers a-n, where a-n represents an integer, each input layer configured to receive observed mmWave radar point cloud data of a respective one of a-n gait characteristics of the subject in motion.

Processor 201 uses executable instructions stored in neural network training module 212 to train a MLNN classifier in accordance with a supervised classification that establishes a correlation between a degenerative condition of the subject as generated at the output layer and the first and at least a second sets of mmWave point cloud data.

In the particular embodiment of a convolution neural network model, the convolution operation typically embodies two parts of inputs: (i) input feature map data, and (ii) a weight (also referred to as output filter, or kernel). Given the input channel data with W(Width)×H(Height)×IC data cube and R×S×IC filter, the output of direct convolution may be formulated as:

$$y_{w,h} = \sum_{r=0}^{R-1}\sum_{s=0}^{S-1}\sum_{c=0}^{C-1} x_{(w+r),(h+s),c} * W_{r,s,c}$$

where:
X=input data/input feature/input feature map
w=width of the input or output data
h=height of the input or output data
R=weight size (width)
S=weight size (height)
C=number of input channel
Y=output data/output feature/output feature map
W=filter/kernel/weight For each input channel, the filter, or weight, are convoluted with data and generates output data. The same location of data of all the input channels are summed together and generate 1 output data channel.

The weight or filter is applied to correlate an anatomical gait dynamics of a subject in motion with a likelihood of a neurodegenerative or muscular degenerative condition being developed, based on an input data stream of mmWave radar point cloud data representing sensed anatomical gait characteristics of the subject's body while in motion.

Each output channel of the convolution model is represented by an output filter or weight used to detect one particular feature or pattern of the input feature data stream. Convolution neural networks constituted of interconnected node assemblies can include many output filters or weights for each layer of the convolution model corresponding to respective features or patterns in the data stream of input features.

In embodiments, training the neural network classifier comprises recursively adjusting the initial matrix of weights by backpropogation in diminishment of a number of the false positive vulnerability defects generated at the output layer in accordance with the supervised classification.

In some embodiments, the backpropagation comprises a backward propagation of errors in accordance with an error matrix as computed at the output layer, the errors being distributed backwards throughout the weights of the at least one neural network intermediate layer.

Processor 201 uses executable instructions stored in neural network trained classifier deployment module 213 to adjust the initial matrix of weights by backpropagation thereby to increase the correlation between the degenerative condition and the first and at least a second sets of mmWave point cloud data.

Methodology

Figure 3:
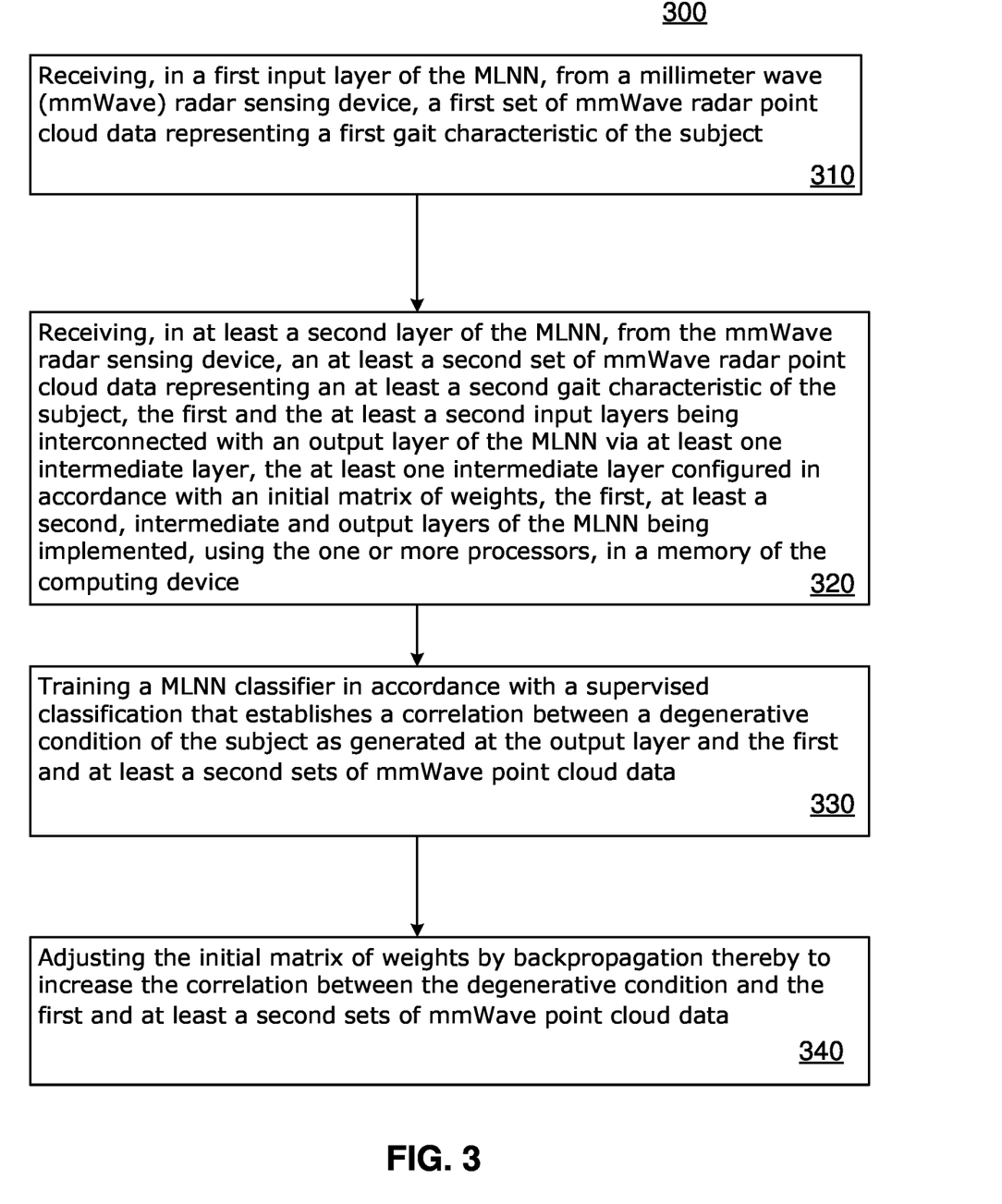
FIG. 3 illustrates a method of operation, in one example embodiment, of a system for training a machine learning neural network (MNLL) in monitoring anatomical gait characteristics.

FIG. 3 illustrates method 300 of operation, in one example embodiment, of a system for training a machine learning neural network (MNLL) in monitoring anatomical gait characteristics, method 300 being performed by one or more processors 201 of server computing device 101. In describing and performing the embodiments of FIG. 3, the examples of FIG. 1 and FIG. 2 are incorporated for purposes of illustrating suitable components or elements for performing a step or sub-step being described.

Examples of method steps described herein relate to the use of server 101 for implementing the techniques described. According to one embodiment, the techniques are performed by anatomical gait monitoring logic module 105 of server 101 in response to the processor 201 executing one or more sequences of software logic instructions that constitute anatomical gait monitoring logic module 105.

In embodiments, anatomical gait monitoring logic module 105 includes the one or more sequences of instructions within sub-modules including mmWave radar point cloud data module 210*a-n*, neural network training module 212 and NN trained classifier deployment module 213. Such instructions may be read into memory 202 from machine-readable medium, such as memory storage devices. In executing the sequences of instructions contained in mmWave radar point cloud data module 210, neural network training module 212 and NN trained classifier deployment module 213 of anatomical gait monitoring logic module 105 in memory 202, processor 201 performs the process steps described herein. In alternative implementations, at least some hard-wired circuitry may be used in place of, or in combination with, the software logic instructions to implement examples described herein. Thus, the examples described herein are not limited to any particular combination of hardware circuitry and software instructions.

At step 310, processor 201 executes instructions of mmWave radar point cloud data module 210 to receive, in a first input layer of the MLNN, from a millimeter wave (mmWave) radar sensing device, a first set of mmWave radar point cloud data representing a first gait characteristic of the subject.

At step 320, processor 201 of server computing device 101 executes instructions, in some embodiments generally concurrently with step 210, to receive, in at least a second layer of the MLNN, from the mmWave radar sensing device, an at least a second set of mmWave radar point cloud data representing an at least a second gait characteristic of the subject, the first and the at least a second input layers being interconnected with an output layer of the MLNN via at least one intermediate layer. The at least one intermediate layer can be configured in accordance with an initial matrix of weights, and the first, at least a second, intermediate and output layers of the MLNN being implemented, using the one or more processors, in a memory of the computing device. mmWave data module 210*a-n*, in embodiments, can be configured with variable numbers of input layers a-n, where a-n represents an integer, each input layer configured to receive observed mmWave radar point cloud data of a respective one of a-n gait characteristics of the subject in motion.

In embodiments, the first and the at least a second gait characteristics are characterized in accordance with at least one of: gait rhythmicity, bilateral stepping coordination, step length scaling, arm swing coordination, arm swing velocity and dynamic postural stability. Dynamic postural stability may be measured relative to a geometrical center of gravity of the subject and reflect the degree to which the subject in motion tends to be off-balance when in motion, such as leaning forwards, backwards, or to the sides.

In some aspects, the first and the at least a second gait characteristics are monitored via the mmW radar sensor device for the subject in motion. The motion as monitored may be include alterations in gait speed, head turns of the subject, avoiding an obstacle by walking around, avoiding an obstacle by stepping over, ascending and descending steps, walking on a bare surface along a corridor, walking on a covered surface along a corridor, and motion in performance of functional mobility tasks in a residence environment.

Gait tendencies, abnormalities or disorders can have distinctive features and are often named to reflect the prominent characteristics of the subject's walk. Gait features representing gait dynamics can be derived from the time series of swing intervals and stance intervals of the left and right feet as represented by the point cloud data. For instance, the gait characteristics may be classified in accordance a hemiplegic gait, in which the subject stands with unilateral weakness on the affected side, arm flexed, adducted and internally rotated. Subjects with a Parkinsonian gait usually take small, shuffling steps. Other gait classifications may include a propulsive gait, where the posture is hunched over and rigid with the head and neck bent forward. Another gait classification may be a scissors gait, where the legs flex slightly at the hips and knees, giving the appearance of crouching, with the knees and thighs hitting or crossing in a scissor-like movement. In a spastic gait, the legs are stiff and the feet drag. In a steppage or scaling gait, the toes scrape the ground while walking. A waddling gait is duck-like. Other gait classifications may include a diplegic gait, a neuropathic gait, a myopathic gait, a choreiform gait, an ataxic gait, a reduced gait and a sensory gait.

A person's manner of walking or gait can correlate to disturbances involving motor, sensory, visual, vestibular, cerebellar, cognitive, psychological and musculoskeletal systems. For example, people in the later stages of Alzheimer's often have "reduced gait," meaning their ability to lift their feet as they walk has diminished. Gait characteristics as observed and monitored may be based on stance, posture, base (wide or narrow), gait initiation (including start hesitation or freezing), walking speed, stride length, step height, foot clearance, continuity, symmetry, trunk sway, path deviation, arm swing. Other gait characteristics may be observed as involuntary movements (e.g., tremor, chorea, dystonia), the ability to turn, the ability to walk on heels and toes and squat, and the ability to rise from a chair without using the arms.

At step 330, processor 201 executes instructions included in neural network training module 212 to train a MLNN classifier in accordance with a supervised classification that establishes a correlation between a degenerative condition of the subject as generated at the output layer and the first and at least a second sets of mmWave point cloud data representative of respective gait characteristics.

At step 340, processor 210 executes instructions included in neural network trained classifier deployment module 213 to adjust the initial matrix of weights by backpropagation thereby to increase the correlation between the degenerative condition and the first and at least a second sets of mmWave point cloud data.

In embodiments, the backpropogation comprises recursively adjusting the initial matrix of weights in diminishment of an error matrix calculated at the output layer thereby to increase the correlation between the likelihood of formation of a neurodegenerative or muscular degenerative condition and the first and at least a second sets of mmWave point cloud data.

In some aspects, measurable or observable parameters, features and characteristics corresponding to the gait patterns can include motion, postural balance about an estimated center of gravity of the subject, arm swing velocity and body balance with regard to both upper body and lower body of human subjects. In embodiments, motion vectors and posture vectors are computed based on sensed mmWave point cloud data representing observed upper and lower body members and body segments of the subjects exhibiting known gait patterns, and gait features representing gait dynamics are derived from observed time series of swing intervals and stance intervals of the left and right lower body members.

In some embodiments, the mmWave radar sensing device comprises a 60 GHz mmWave radar sensing device.

The neural networks of embodiments herein refer to an artificial intelligence (AI) based neural network, including machine learning (ML) or deep learning (DL) models, constituted of interconnected nodes, and assemblies of nodes. In a particular embodiment, the ML or neural network model herein may be implemented as a convolution neural network (CNN).

Figure 4:
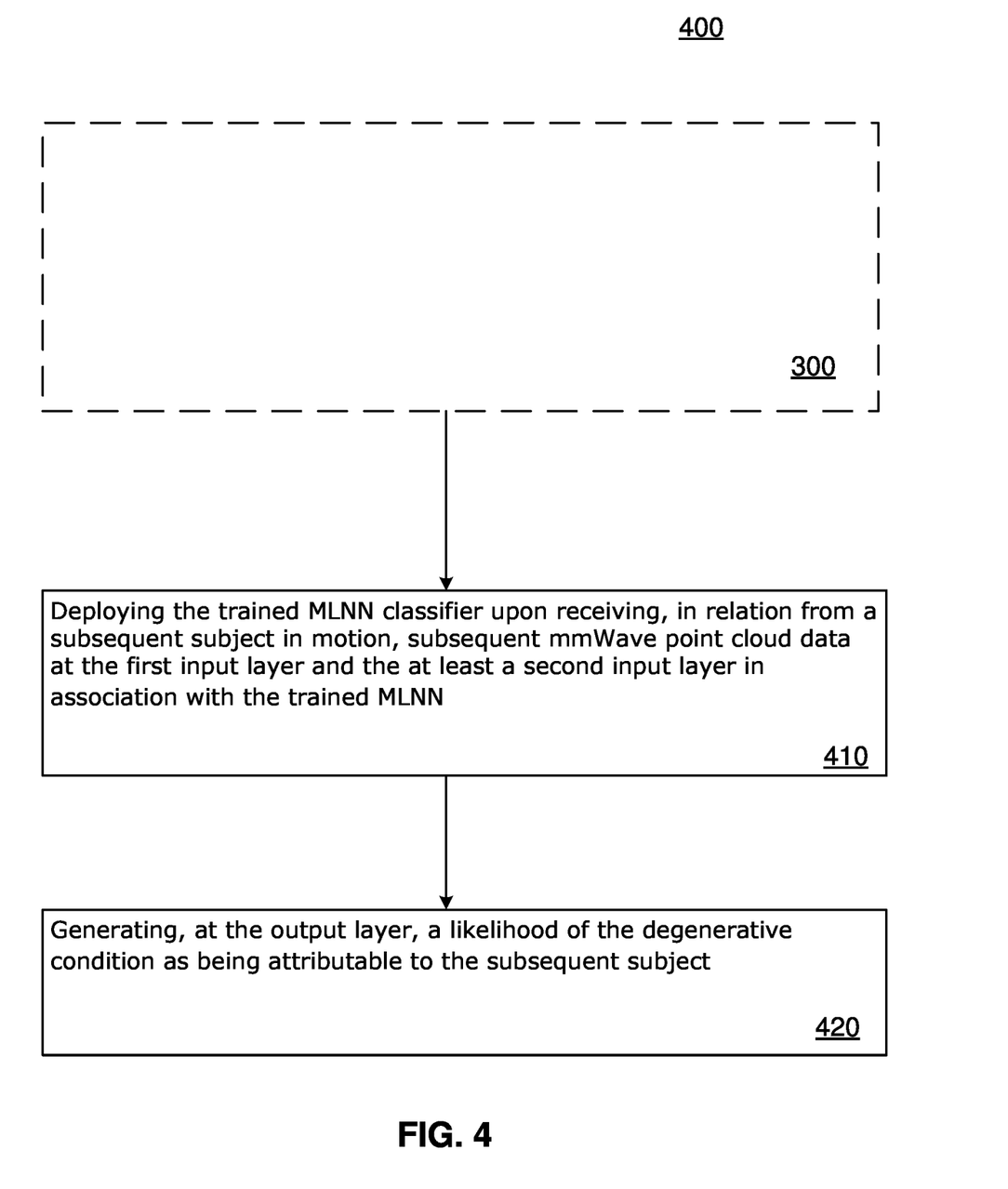
FIG. 4 illustrates a method of operation, in one example embodiment, for deploying a trained machine learning neural network (MNLL) in predicting patient degenerative conditions based on anatomical gait characteristics.

FIG. 4 illustrates method 400 of operation, in one example embodiment, for deploying a trained machine learning neural network (MNLL) in predicting patient degenerative conditions based on anatomical gait characteristics, using the trained classifier in conjunction with the disclosures of FIGS. 1-3. In some aspects, such deploying proceeds once the trained classifier, based on the supervised training as described herein with regard to FIG. 3, for example, produces a sufficiently high correlation in predicting formation and onset of neurodegenerative or muscular degenerative conditions or states with high enough accuracy of prediction. In one embodiment, the deploying proceeds when the trained classifier attains at least a threshold limit of 90 percent likelihood of predicting formation of a degenerative condition.

At step 410, deploying the trained MLNN classifier upon receiving, in relation from a subsequent subject in motion, subsequent mmWave point cloud data at the first input layer and the at least a second input layer in association with the trained MLNN.

At step 420, generating, at the output layer, a likelihood of the degenerative condition as being developed by, and attributable to, the subsequent subject.

In some alternate embodiments, the system 100 can automatically detect gradual or sudden onset movement pattern abnormalities. If, for example for the last 30 days the patient is walking normally but suddenly on one day he is walking very slow or the gait is staggered, it might be because the patient is experiencing subtly changed impaired mobility because of an injury, infection, fever or even early stages of a stroke. Similarly, system 100 can detect, based on averaging of prior results during a training regimen for a particular human subject, that the movement pattern based on gait characteristics from point cloud data for the previous 90 days is statistically different from the pattern in a more recent period, say for the last 10 to 20 days. In such alternate embodiments, system 100 is not limited to detecting results based on pretrained models, but additionally, enables detection of gait characteristic anomalies that are observed to have developed, or be developing, over a relatively shorter period of time, for instance ranging from 1 to 3 weeks in some embodiments. In this manner, by applying statistical measures including mean and averages, including moving averages of previously observed point cloud data, the human subject can detected as manifesting a movement pattern anomaly where gait characteristics for a previous period is statistically different from the movement pattern observed over a more recent portion of that previous period.

In the deployment, one aspect provides for tracking multiple patients based on a respective patient ID assigned in conjunction with their respective mmWave radar signature (point cloud and density) and one or more of a patient age, weight, blood pressure, height, sex, pulse rate, and any physical profile parameter inherent to an individual patient. This way a single mmWave radar unit can monitor gait dynamics and postural characteristics of multiple patients in a controlled setting, such as in a ward or ICU hospital or medical clinic setting.

It is contemplated that embodiments described herein extend to individual elements and concepts described herein, as well as for embodiments to include combinations of elements, features and techniques recited herein. Although embodiments are described in detail herein with reference to the accompanying drawings, it is to be understood that the invention is not limited to only such example embodiments. Accordingly, many modifications and variations will be apparent to practitioners skilled in the art. As such, it is intended that the scope of the invention be defined by the following claims and their equivalents. Furthermore, it is contemplated that a particular feature described either individually or as part of an embodiment can be combined with other individually described features, or parts of other embodiments, even if the other features and embodiments make no mention of the particular feature. Thus, absence of particular describing combinations does not preclude the inventors from claiming rights to such combinations.

What is claimed is:

1. A method of training a machine learning neural network (MLNN), the method performed in one or more processors and comprising:
receiving, in a first input layer of the MLNN, from a millimeter wave (mmWave) radar sensing device, a first set of mmWave radar point cloud data representing a first gait characteristic of a subject in motion, the first gait characteristic comprising an arm swing velocity;
receiving, in at least a second layer of the MLNN, from the mmWave radar sensing device, an at least a second set of mmWave radar point cloud data representing an at least a second gait characteristic comprising a measure of dynamic postural stability that is indicative of a degree to which the subject in motion is off-balance, the first and the at least a second input layers being interconnected with an output layer of the MLNN via at least one intermediate layer, the first, at least a second, intermediate and output layers of the MLNN being instantiated, using the one or more processors, in a memory of a computing device; and
training a MLNN classifier in accordance with a classifier that increases a correlation between a degenerative condition of the subject as generated at the output layer and the first and at least a second sets of mmWave point cloud data.

2. The method of claim 1 wherein the at least one intermediate layer is configured in accordance with an initial matrix of weights, and further comprising increasing the correlation in accordance with adjusting the initial matrix of weights by backpropagation.

3. The method of claim 2 wherein the backpropagation comprises recursively adjusting the initial matrix of weights in diminishment of an error matrix calculated at the output layer thereby to increase the correlation between the degenerative condition and the first and at least a second sets of mmWave point cloud data.

4. The method of claim 1 wherein the first and the at least a second gait characteristics are monitored via the mmWave radar sensing device for the subject in motion, where the motion includes at least one of: alterations in gait speed, head turns of the subject, avoiding an obstacle by walking around, avoiding an obstacle by stepping over, ascending and descending steps, walking on a bare surface along a corridor, walking on a covered surface along a corridor, and motion in performance of functional mobility tasks in a residence environment.

5. The method of claim 1 wherein the first and the at least a second gait characteristics are classified in accordance with at least one of: a hemiplegic gait, a diplegic gait, a neuropathic gait, a myopathic gait, a choreiform gait, an ataxic gait, a Parkinsonian gait, a reduced gait and a sensory gait.

6. The method of claim 1 wherein the degenerative condition of the subject comprises at least one of a neuro-degenerative condition and a muscular dystrophy condition.

7. The method of claim 1 wherein, during the training, the subject is detected as manifesting a movement pattern anomaly in point cloud data where gait characteristics for a previous period is statistically different from the movement pattern observed over a more recent period as compared with the previous period.

8. The method of claim 1 further comprising deploying the trained MLNN classifier in predicting a degenerative condition upon establishing the correlation with the degenerative condition exceeds a predetermined percentage threshold value.

9. The method of claim 8 further comprising deploying the trained MLNN classifier in predicting a likelihood of the degenerative condition upon receiving, from a subsequent subject in motion, subsequent mmWave point cloud data at the first input layer and the at least second input layer in association with the trained MLNN.

10. The method of claim 1 wherein the measure of dynamic postural stability is established relative to a geometrical center of gravity that is indicative of a degree to which the subject in motion is off-balance in accordance with at least one of leaning forwards, backwards, and laterally.

11. A computing system comprising:
one or more processors;
a memory storing a set of instructions, the instructions when executed in the one or more processors causing operations including:
receiving, in a first input layer of a machine learning neural network (MLNN), from a millimeter wave (mmWave) radar sensing device, a first set of mmWave radar point cloud data representing a first gait characteristic of a subject in motion, the first gait characteristic comprising an arm swing velocity;
receiving, in at least a second layer of the MLNN, from the mmWave radar sensing device, an at least a second set of mmWave radar point cloud data representing an at least a second gait characteristic comprising a measure of dynamic postural stability that is indicative of a degree to which the subject in motion is off-balance, the first and the at least a second input layers being interconnected with an output layer of the MLNN via at least one intermediate layer, the first, at least a second, intermediate and output layers of the MLNN being instantiated, using the one or more processors, in the memory; and
training a MLNN classifier in accordance with a classifier that increases a correlation between a degenerative condition of the subject as generated at the output layer and the first and at least a second sets of mmWave point cloud data.

12. The computing system of claim 11 wherein the at least one intermediate layer is configured in accordance with an initial matrix of weights, and further comprising instructions executable in the one or more processors to increase the correlation in accordance with adjusting the initial matrix of weights by backpropagation.

13. The computing system of claim 12 wherein the backpropagation comprises recursively adjusting the initial matrix of weights in diminishment of an error matrix calculated at the output layer thereby to increase the correlation between the degenerative condition and the first and at least a second sets of mmWave point cloud data.

14. The computing system of claim 11 wherein the first and the at least a second gait characteristics are monitored via the mmWave radar sensing device for the subject in motion, where the motion includes at least one of: alterations in gait speed, head turns of the subject, avoiding an obstacle by walking around, avoiding an obstacle by stepping over, ascending and descending steps, walking on a bare surface along a corridor, walking on a covered surface along a corridor, and motion in performance of functional mobility tasks in a residence environment.

15. The computing system of claim 11 wherein the first and the at least a second gait characteristics are classified in accordance with at least one of: a hemiplegic gait, a diplegic gait, a neuropathic gait, a myopathic gait, a choreiform gait, an ataxic gait, a Parkinsonian gait, a reduced gait and a sensory gait.

16. The computing system of claim 11 wherein the degenerative condition of the subject comprises at least one of a neurodegenerative condition and a muscular dystrophy condition.

17. The computing system of claim 11 wherein, during the training, the subject is detected as manifesting a movement pattern anomaly in point cloud data where gait characteristics for a previous period is statistically different from the movement pattern observed over a more recent period as compared with the previous period.

18. The computing system of claim 11 further comprising deploying the trained MLNN classifier in predicting a degenerative condition upon establishing the correlation with the degenerative condition exceeds a predetermined percentage threshold value.

19. The computing system of claim 11 wherein the measure of dynamic postural stability is established relative to a geometrical center of gravity that is indicative of a degree to which the subject in motion is off-balance in accordance with at least one of leaning forwards, backwards, and laterally.

20. A computer readable non-transitory memory storing instructions, the instructions when executed in a processor causing the processor to implement operations comprising:
receiving, in a first input layer of a machine learning neural network (MLNN), from a millimeter wave (mmWave) radar sensing device, a first set of mmWave radar point cloud data representing a first gait characteristic of a subject in motion, the first gait characteristic comprising an arm swing velocity;

receiving, in at least a second layer of the MLNN, from the mmWave radar sensing device, an at least a second set of mmWave radar point cloud data representing an at least a second gait characteristic comprising a measure of dynamic postural stability that is indicative of a degree to which the subject in motion is off-balance, the first and the at least a second input layers being interconnected with an output layer of the MLNN via at least one intermediate layer, the first, at least a second, intermediate and output layers of the MLNN being instantiated, using the one or more processors, in a memory of a computing device; and training a MLNN classifier in accordance with a classifier that increases a correlation between a degenerative condition of the subject as generated at the output layer and the first and at least a second sets of mmWave point cloud data.

\* \* \* \* \*